United States Patent
McCall et al.

(10) Patent No.: US 6,591,239 B1
(45) Date of Patent: Jul. 8, 2003

(54) VOICE CONTROLLED SURGICAL SUITE

(75) Inventors: David F. McCall, Edinboro, PA (US);
Leslie M. Logue, Edinboro, PA (US);
Francis J. Zelina, Lake City, PA (US);
Matthew V. Sendak, Montgomery, AL (US); Julie R. Hinson, Concord, OH (US); Ward L. Sanders, Albion, PA (US); Steve Belinski, Santa Barbara, CA (US); Brian E. Holtz, Santa Barbara, CA (US)

(73) Assignee: Steris Inc., Temecula, CA (US)

(*) Notice: Subject to any disclaimer, the term of this patent is extended or adjusted under 35 U.S.C. 154(b) by 0 days.

(21) Appl. No.: 09/458,175

(22) Filed: Dec. 9, 1999

(51) Int. Cl.7 .......................... G10L 15/22; A61B 17/00
(52) U.S. Cl. ........................ 704/275; 704/270; 340/3.5
(58) Field of Search ................................ 704/275, 270; 340/3.5

(56) References Cited

U.S. PATENT DOCUMENTS

| | | | |
|---|---|---|---|
| 4,158,750 A | | 6/1979 | Sakoe et al. |
| 4,207,959 A | | 6/1980 | Youdin et al. |
| 4,641,292 A | | 2/1987 | Tunnell et al. |
| 4,776,016 A | | 10/1988 | Hansen |
| 4,807,273 A | | 2/1989 | Haendle |
| 4,989,253 A | * | 1/1991 | Liang et al. ................. 381/110 |
| 5,230,023 A | | 7/1993 | Nakano |
| 5,274,862 A | | 1/1994 | Palmer, Jr. et al. |
| 5,303,148 A | | 4/1994 | Mattson et al. |
| 5,335,313 A | * | 8/1994 | Douglas ....................... 704/275 |
| 5,345,538 A | | 9/1994 | Narayannan et al. ...... 395/2.84 |
| 5,372,147 A | | 12/1994 | Lathrop, Jr. et al. ........ 128/898 |
| 5,511,256 A | | 4/1996 | Capaldi |
| 5,566,272 A | | 10/1996 | Brems et al. |
| 5,572,999 A | | 11/1996 | Funda et al. ............. 128/653.1 |
| 5,715,548 A | | 2/1998 | Weismiller et al. |
| 5,729,659 A | | 3/1998 | Potter |
| 5,771,511 A | | 6/1998 | Kummer et al. |
| 5,788,688 A | | 8/1998 | Bauer et al. ..................... 606/1 |
| 5,809,591 A | | 9/1998 | Capaldi et al. |
| 5,812,978 A | | 9/1998 | Nolan |
| 5,841,950 A | | 11/1998 | Wang et al. |
| 5,884,350 A | | 3/1999 | Kurze |
| 5,970,457 A | * | 10/1999 | Brant et al. .................. 704/275 |
| 6,224,542 B1 | * | 5/2001 | Chang et al. ................ 600/109 |
| 6,278,975 B1 | * | 8/2001 | Brant et al. .................. 704/275 |

FOREIGN PATENT DOCUMENTS

| | | | |
|---|---|---|---|
| WO | WO 96/09587 | 3/1996 | |
| WO | WO 97/49340 | * 12/1997 | ........... A61B/17/00 |
| WO | WO 99/21165 | 4/1999 | |

* cited by examiner

Primary Examiner—Tālivaldis Ivars Šmits
(74) Attorney, Agent, or Firm—Fay, Sharpe, Fagan, Minnich & McKee, LLP

(57) ABSTRACT

A voice controlled surgical suite is provided for controlling a plurality of surgical apparatus by a single human. The system includes a voice recognition device adapted to recognize a plurality of predetermined speech commands from a single human and to generate a corresponding set of command output signals. A surgical table is operatively connected with the voice recognition device and is responsive to a first set of the command output signals to initiate selected surgical table movements. A surgical lighthead is similarly connected with the voice recognition system and is responsive to a second set of the command output signals to initiate selected surgical lighthead operations. In addition, surgical camera and task light devices are included in the system and are responsive to fourth and third sets of command output signals, respectively, generated by the voice recognition device to initiate selected surgical camera and surgical task light operations. The surgical apparatus has manual controls to provide redundancy, and to override voice control signals as needed.

16 Claims, 8 Drawing Sheets

VOICE CONTROLLED SURGICAL SUITE

BACKGROUND OF THE INVENTION

The present invention is directed to the art of medical equipment and, more particularly, to a system of voice controlled surgical equipment of the type used in an operating room for performing surgical procedures. The present invention will be described with particular reference to a voice controlled integrated surgical suite including at least a surgical table and a surgical lighthead device. In another embodiment, the integrated voice controlled suite includes surgical table and lighthead devices and, in addition, a voice controlled surgical task light and a voice commanded video camera incorporated into the lighthead. It should be understood, however, that the invention has broader application and uses in the medical arts as well as in industrial processes, or anywhere there is a need for speech recognition control by a human operator over a plurality of integrated voice-controllable devices.

Nearly all surgical procedures are performed in an operating room on a surgical table. The tables have been developed over the years into highly specialized apparatus including a patient support surface forming various head and foot sections which are movable relative to a central support surface. In addition, the patient support surface itself is typically positionable relative to a base or pedestal portion of the surgical table. The capacity to execute all of the above motions and articulations and others are typically incorporated into standard surgical tables to enable the tables to be used in a wide range of surgical procedures to best support the patient in one or more desired positions.

Typically, modern surgical tables include a manually operable control device or pendant connected to the table by means of an elongate flexible electrical cable. The control device often includes a plurality of switches and actuators that enable the surgeon or other operating room personnel to control mechanisms within the table to achieve the selected motions or operations. Oftentimes, the control pendant includes one or more visual indicia for reporting the status of certain features of the surgical table to a human operator. As an example, one important visual indicia is used to report the status of the surgical table floor locks, particularly when they are in an unlocked state. The floor locks must be activated before any further table motion is permitted and before surgery can be performed.

In the past, the task of manually actuating the control pendant has been placed on the shoulders of the anesthesiologist. One reason for this is that the elevation of the patient's feet relative to his head must be controlled and adjusted during the administration of anesthesia. Another reason for the anesthesiologist to be handed the pendant control task is to maintain the integrity of the sterile field. More particularly, the control device typically hangs on a side rail of the surgical table but can be extended beyond the rail confines by paying out additional cable lengths. The area beyond the side rail is not in the sterile field. Accordingly, in order for the surgeon to use the control device, he must hold it and/or keep it within the sterile field at all times. Of course, this is inconvenient and could compromise the results of the surgical procedure.

In addition to the above, although sterile bags could be placed over the control device, the bags make manipulation of the switches and other actuators on the control device difficult and distracting to the surgeon. Primarily, bags have been used on control devices to protect the devices themselves from various fluids that might be inadvertently splashed on the control device during a procedure. Typically, therefore, the bags are used more for protecting the control pendant from contamination rather than protecting the sterile field from contamination by the control pendant.

One major problem that arises during surgical procedures is squarely centered on the cumbersome nature and inconvenience of the manual control pendant used with most surgical tables. More particularly, whenever a surgeon desires a patient to be moved from a first position to a second position, the surgeon must verbally call out such order to the control pendant attendant. When the surgeon and attendant are well rehearsed, the table movement can be executed with relative ease. However, commands from the surgeon to the attendant are not always perfect. Intellectual misunderstandings occur and oftentimes language barriers exist. Further, surgeons often wear masks making their speech difficult to understand.

Another problem with table motion based on a surgeon's verbal commands arises due to the delay time between the command utterance, its interpretation, and then eventual implementation. Sometimes it is necessary to move the table into a particular desired orientation in a hurried manner. When that is the case, large delay times between verbal commands and their actual implementation can be dangerous to the patient.

In addition to surgical tables, lightheads are also necessary during surgical procedures. To that end, typical lightheads include a sterile manual handle portion to enable surgeons to reach overhead, grasp the handle, and then manually move the lighthead into a desired position and orientation. Light intensity and ON/OFF operations, however, are typically controlled from a remote wall unit. Again, since the wall unit is typically not located within the sterile field, the surgeon must rely on the assistance of other operating room personnel to change the lighthead operation parameters in order to preserve the integrity of the sterile field.

Electronic video cameras have been used to film surgical procedures and provide live video images of the procedures for purposes of training and the like. These video cameras have often been controlled by additional operating room personnel, by an operator at a remote location, or by the surgeon using a footswitch device or the like. Typical footswitch controls include zoom in/out and rotate CW/CCW.

It has been found that the footswitches add unnecessary clutter to the critical floor space adjacent the surgical table. This can lead to very undesirable results should the surgeon trip on the footswitch or otherwise experience a misstep.

In all of the above, additional personnel are needed to effect the manual operation of the operating room support devices. These personnel add costs to the procedure and place a burden on operating room resources such as floor space and room ventilation and cooling apparatus.

Therefore, it is desirable to provide a system for enabling a human operator such as surgeon, to control a suite of operating room equipment without compromising the sterile field. Preferably, the suite of equipment is voice controlled based on speech recognition.

It is also desirable to reduce the chance of the occurrence of error in surgical table positioning. It is preferable that the surgical table be controlled directly by the surgeon but in a manner without compromising the sterile field such as by hands free control.

Still further, it is also desirable for the surgeon to directly control surgical lightheads, surgical cameras, and other devices in the operating room to reduce the number of auxiliary personnel and other clutter that is otherwise needed to adjust and control these devices.

SUMMARY OF THE INVENTION

In accordance with the present invention, a system for controlling a plurality of surgical apparatus by a human operator is provided. The system includes a speech recognition device adapted to recognize a plurality of predetermined voice commands from the human operator. Further, the voice controlled system is responsive to a set of predetermined voice commands to generate a corresponding set of command output signals. A surgical table is operatively connected with the speech recognition system and is responsive to a first set of the command output signals to initiate selected surgical table movements. A surgical lighthead is also operatively connected with the speech recognition system and is responsive to a second set of the command output signals to initiate selected surgical lighthead operations.

In accordance with a more detailed aspect of the invention, the voice controlled system is responsive to the set of predetermined voice commands from the human operator to generate various command output signals to generate selected motion in the surgical table including height, Trendelenberg, back, flex, leg, tilt, level, and stop motions. In addition, the system causes voice controlled action in the surgical lighthead including surgical lighthead ON/OFF actions and lighthead intensity responses.

In accordance with a more limited aspect of the invention, the system for controlling a plurality of surgical apparatus includes a surgical camera operatively connected with the speech recognition system. The surgical camera is responsive to a third set of command output signals to initiated selected surgical camera operations.

In accordance with a still further limited aspect of the invention, the subject system includes a surgical task light operatively connected with the speech recognition system. The surgical task light is responsive to a fourth set of the command output signals to initiate selected surgical task light operations.

Further in accordance with the invention, there is provided a method for voice controlling a plurality of surgical apparatus by a human operator. A speech recognition device responsive to a set of predetermined voice commands from the human operator is provided. The voice recognition device generates a set of command output signals. A surgical table is provided and is operatively associated with the speech recognition device and is responsive to a first set of the command output signals to initiate selected surgical table movements. Further, a surgical lighthead is provided and is operatively associated with the speech recognition system. The surgical lighthead is responsive to a second set of the command output signals to initiate selected surgical lighthead operations. The method includes the step of receiving a first voice command from the human operator into the speech recognition system. Thereafter, based on the first voice command, the method includes generating, in the speech recognition system, a one of the first set of the command output signals for initiating the selected surgical table movement and the second set of the command signals for initiating the selected lighthead operations.

In accordance with a more limited aspect of the subject method in accordance with the invention, the method includes the step of providing a surgical camera responsive to a third set of the command output signals to initiate selected camera operations.

In accordance with a further limited aspect of the invention, the method includes the step of providing a surgical task light operatively associated with the speech recognition system and responsive to a fourth set of the command output signals to initiate selected surgical task light operations.

It is a primary advantage of the present invention that a surgical suite including a plurality of apparatus, namely at least a surgical table and a surgical lighthead is voice controlled by a human operator, preferably the surgeon. The subject voice controlled surgical suite enables a more efficient and easier to use set of medical appliances.

The subject system provides the advantage of reducing the number of personnel required to be present during surgical procedures.

Further, the present invention increases the safety of surgical procedures by minimizing the risk of misunderstanding and/or miscommunication of command messages from the surgeon to the support staff. In the subject system, the surgical suite is commanded directly by a surgeon's voice control using word recognition techniques.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, preferred embodiments of which will be described in detail in this specification and illustrated in the accompanying drawings which form a part hereof, and wherein.

DETAILED DESCRIPTION OF THE PREFERRED EMBODIMENT

Figure 1:
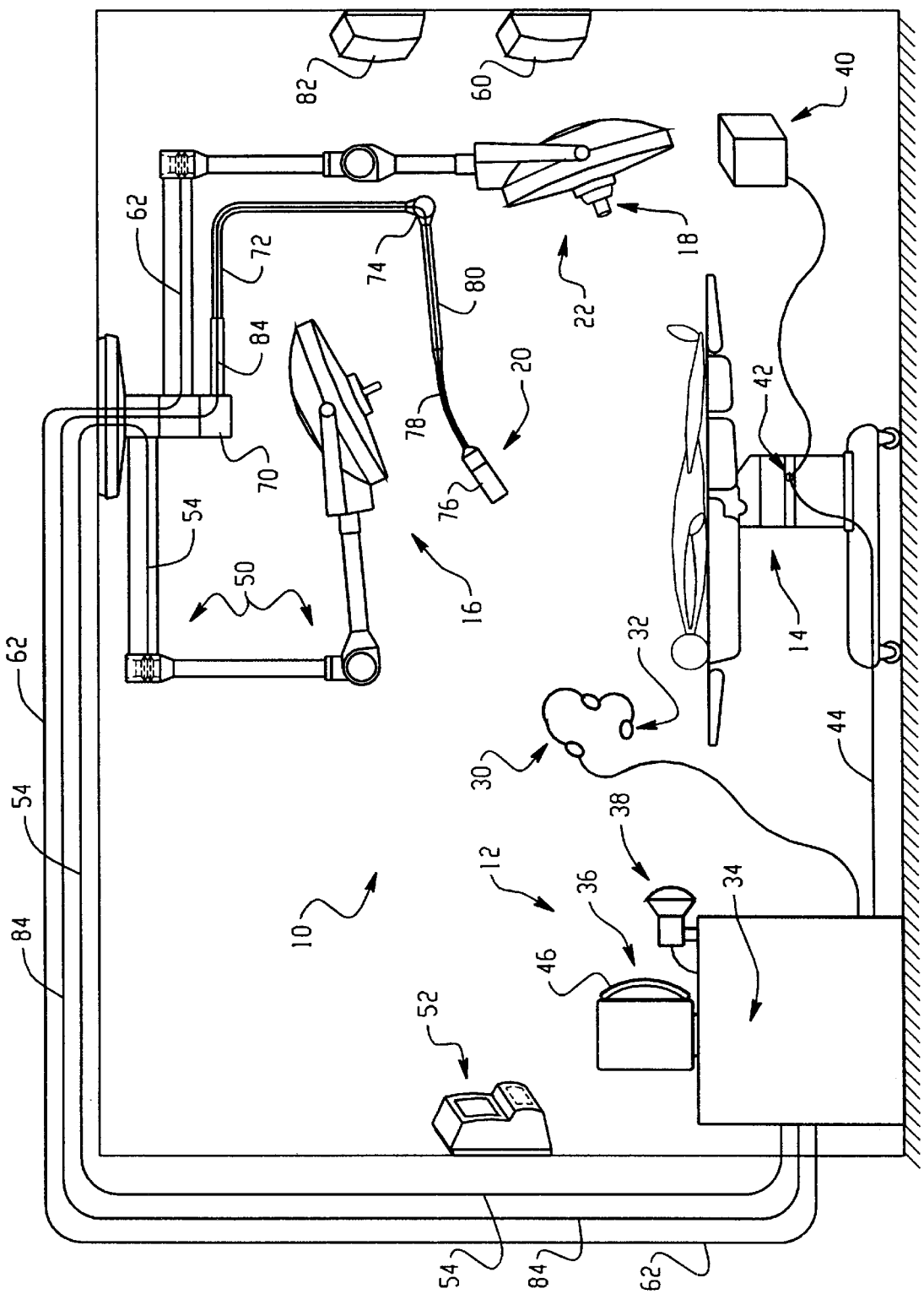
FIG. 1 is a schematic view of a surgical room including the voice controlled surgical suite formed in accordance with the present invention.

Referring now to the drawings wherein the showings are for the purposes of illustrating the preferred embodiments of the invention only and not for purposes of limiting same, FIG. 1 shows a voice controlled surgical suite 10 formed in accordance with the present invention. As shown, the system 10 includes a speech recognition device 12 adapted to recognize a plurality of predetermined voice commands from a human operator. The speech recognition device 12 is responsive to the set of predetermined voice commands to generate a set of command output signals in a manner to be described in greater detail below. The system 10 further includes a surgical table 14 operatively connected with the speech recognition device 12. The table 14 is responsive to a first set of the command output signals generated by the speech recognition device 12 to initiate selected surgical table movements. Further, the system 10 includes a surgical lighthead 16 operatively connected with the speech recognition device 12. The surgical lighthead is responsive to a second set of the command output signals generated by the speech recognition device 12, preferably power ON/OFF commands and light intensity commands, to initiate selected surgical lighthead operations.

With continued reference to FIG. 1, the voice controlled surgical suite 10 further includes a surgical camera 18 operatively connected with the speech recognition device 12. The surgical camera 18 is responsive to a third set of the command output signals generated by the speech recognition device 12 to initiate selected surgical camera operations. Preferably, the camera operations include camera power ON/OFF operations, zoom IN/OUT operations and camera rotate CW/CCW operations.

In addition, the subject voice controlled surgical suite 10 includes a surgical task light 20 operatively connected with the speech recognition device 12. The surgical task light 20 is responsive to a fourth set of the command output signals to initiate selected surgical task light operations, preferably, power ON/OFF and light intensity operations.

Preferably, the speech recognition device 12 includes a headset 30 adapted to be worn by a surgeon during surgical procedures. The headset 30 includes a microphone 32 for receiving oral instructions from the surgeon and delivering the oral instructions to a processing unit 34 disposed near the subject system 10. Preferably, the processing unit 34 includes software and related hardware for receiving and interpreting oral commands from a surgeon and generating appropriate corresponding output signals. Such processing units are found in the art and are readily available. However, one preferred processing unit is manufactured by Computer Motion of California.

A display 36 is operatively connected to the processing unit 34 together with a pair of sound generating devices, preferably speakers 38. The display 36 is adapted to receive display command signals from the processing unit 34 for generating graphical representations of the operations of selected portions of the subject system. The graphical output that is manifested on the display 36 enables a surgeon to confirm the successful interpretation and/or completion of verbal commands spoken into the microphone 32. Similarly, the sound generating devices 38 are used by the speech recognition device 12 to generate audio signals that are useful by a surgeon to confirm the successful receipt and interpretation of verbal commands spoken into the microphone 32.

With continued reference to FIG. 1, the surgical table 14 comprising the subject voice controlled surgical suite 10 includes a manually operable control pendant 40. The control pendant 40 enables the control and positioning of various portions of the table into selected desired positions and/or orientations in a manner as described above. To that end, the control pendant 40 used in the subject system is essentially known in the art.

However, the surgical table 14 includes an additional parallel input port 42 for connection to a table command signal line 44 for interconnecting the surgical table 14 with the voice recognition device 12. Preferably, the table command signal line 44 is essentially connected in parallel with the control pendant 40 so that control circuitry (not shown) within the surgical table 14 can react to commands received from the speech recognition device 12 substantially in a manner as they are executed when originating from the control pendant 40. In the preferred embodiment, therefore, the processing unit 34 generates signals having an identical protocol as the signals generated from the control pendant 40. In that way, minimal modification to the hardware and/or software control of the surgical table 14 is necessary to adapt the table for use in the subject voice controlled surgical suite 10. Also, preferably, the surgical table is adapted to respond exclusively to the control pendant 40 override command signals when both the pendant override signals and the speech command signals from the speech recognition device are present.

As noted above, the speech recognition device 12 includes a headset 30 connected to a processing unit 34. This enables a surgeon to speak into the microphone 32 so that the surgeon's speech is received and interpreted by the processing unit 34 to generate the appropriate output signals for control over one or more of the table, lighthead, camera, and surgical task light devices. Alternatively, the display 36 includes a touch screen portion 46 to enable the surgeon or other operating room personnel to input command signals into the speech recognition device 12 to control one or more of the surgical table, lighthead, camera, and task light devices.

With yet continued reference to FIG. 1, the surgical lighthead 16 is suspended from overhead by a standard multi-segment surgical lighting support system 50. The support system is movable into a range of positions and orientations to direct the columns of light falling from the surgical lighthead onto the surgical field as needed. The surgical lighthead 16 is operatively connected to a wall control unit 52 for providing a means for manually adjusting the operating conditions of the surgical lighthead. Typically, wall control units 52 include manual power ON/OFF controls. In addition to the above, however, in accordance with the present invention, the surgical lighthead 16 is connected to the processing unit 34 of the speech recognition device 12 using a lighthead command signal line 54. In that way, the surgical lighthead 16 is responsive to commands originating from both the wall control unit 52 and the processing unit 34. To that end, the processing unit 34 is responsive to a predetermined set of voice command signals based on words spoken into the microphone 32.

In addition to the above, a lower surgical lighthead 22 carries a modular digital video camera unit 18 at the center of the lighthead as shown. The video camera unit has the general outward appearance of a standard surgical lighthead handle and can be used to manually manipulate the lower surgical lighthead 22 into operative position relative to the surgical field as needed. Preferably, the modular video camera 18 is selectively actuated using a second wall control unit 60. The second wall control unit includes manual input devices for controlling selected camera operations including camera zoom IN/OUT operations and camera rotate CW/CCW operations.

In addition to the above, the surgical camera 18 is responsive to output command signals generated by the processing unit 34 and placed on camera command signal line 62. In that way, the surgical camera 18 is responsive to commands originating from both the second wall control unit 60 as well as from the processing unit 34.

With still yet continued reference to FIG. 1, the subject voice controlled surgical suite 10 includes a surgical task light 20 provided as an auxiliary lighting system to augment the illumination developed by the first and second surgical lightheads 16, 22. The task light 20 may also be used by itself or with a single surgical lighthead. Preferably, the task light generates a cold beam of light having a spot size between two and six inches.

The task light 20 is supported from the ceiling by a mechanical rotary hub member 70 that is freely movable through multiple rotations without mechanical binding or interference so that the task light supported therefrom can be moved into any desirable orientation. An elongate L-shaped support member 72 is connected on one end to the mechanical rotary hub member 70 and, on the other end, to a mechanical compound counterbalanced joint member 74. The L-shaped member 72 is substantially hollow to enable an elongate fiber optic cable (not shown) to be carried therein. In that way, the fiber optic cable is concealed and protected within the L-shaped support member and below.

The lower portion of the fiber optic task light system 20 includes a manual zoom lens device 76 carried on a flexible gooseneck 78 which is in turn supported from the mechanical counterbalanced joint member 74 by a rigid elongate support member 80. The support member and flexible gooseneck carry the lower portion of the fiber optic cable so that the mechanical zoom lens device 76 can be used to emit light from a distal end of the task light 20 onto the surgical site.

The operation of the task light 20 is controlled from a third wall control unit 82 by personnel within the operating room. Preferably, the operations include power ON/OFF. In addition, the task light is responsive to output signals generated by the processing unit 34 and carried on a task light command signal line 84. In that way, the task light is responsive to commands originating from both the third wall control unit 82 as well as from the processing unit 34.

Figure 2:
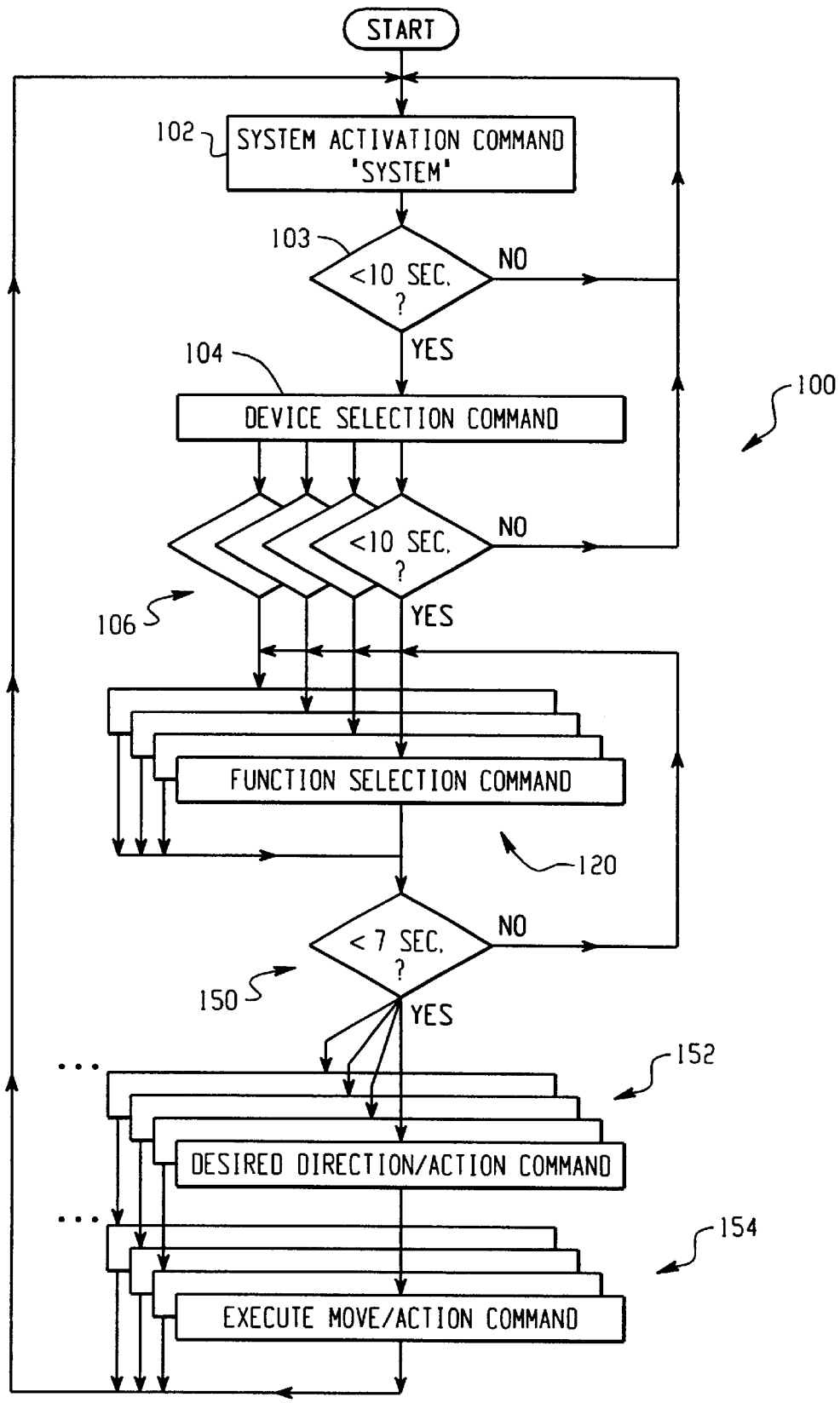
FIG. 2 is a flowchart showing the overall high level view of the control processing executed by the voice controlled surgical suite of FIG. 1.

FIG. 2 illustrates the preferred surgical suite control method 100 in accordance with the present invention. Turning now to that figure, the system 10 is responsive to a system actuation command spoken into the microphone 32. In that regard, at step 102, the system 10 receives the spoken system actuation command "SYSTEM". When the word "SYSTEM" is spoken into the microphone 32, the processing unit 34 processes the spoken command and interprets same as being the system actuation command. Preferably, the system 10 remains idle until the selected system actuation command is received. Thereafter, the system awaits, in step 104, a device selection command. In step 103 the system includes a time out counter so that if no device selection command is received within a predetermined delay period, the system resets to a state of awaiting the system activation command "SYSTEM".

As noted above, the subject voice controlled surgical suite 10 includes a plurality of voice controlled devices including a surgical table, lighthead, camera, and task light. Accordingly, in the device selection command step 104, the processing unit 34 interprets the words spoken into the microphone 32 for determining which of the plurality of devices 14, 16, 18, or 20 are to be controlled using spoken word commands.

It is an advantage of the present invention that the surgical suite control method 100 is hierarchical in nature. More particularly, spoken word commands intended for actuation of the surgical table are not confused with commands intended for any of the other devices forming the surgical suite. As will be described in greater detail below, the command control flow passes through the device selection command step 104 whereat the system enters into one of several modes, for example, a "table control" mode. Other preferred examples include a "lighthead control" mode, a "task light control" mode, and a "camera control" mode. The several modes of operation ensure a separation between function selection commands and desired direction/operation commands in the various devices. In addition, this prevents cross interpretation between commands meant for the various devices.

It is another advantage of the present invention that the subject control method 100 includes a set of safety features including a first delay reset step 106 whereat the control method is returned to the system activation command step 102 when, after a valid device selection command is received at step 104, the command is thereafter followed by a pause time of about ten seconds.

Figure 3:
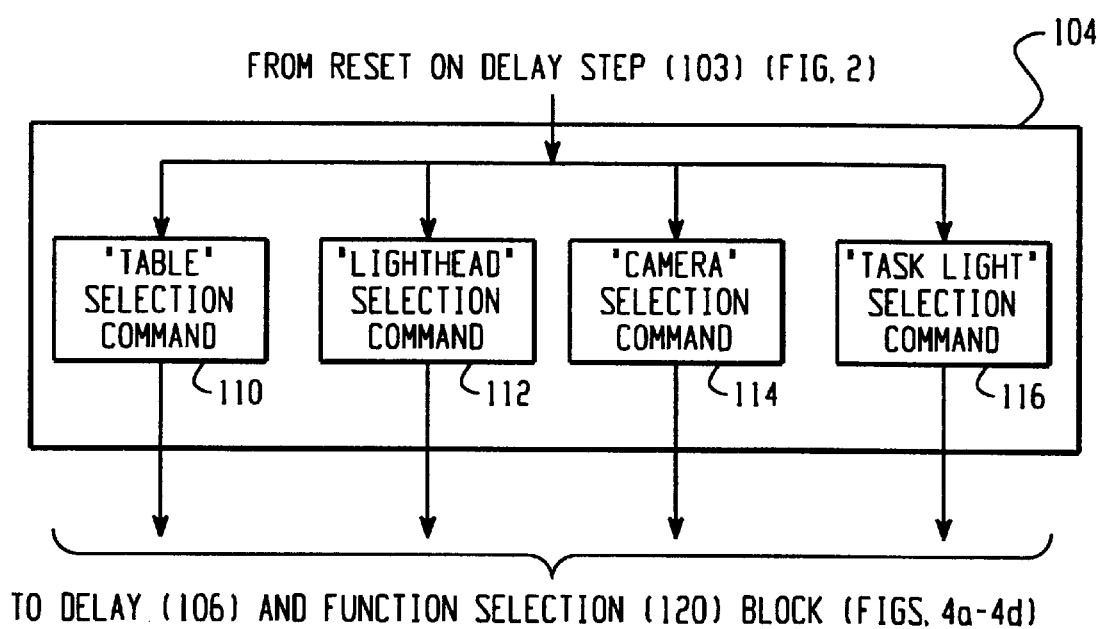
FIG. 3 is a flowchart illustrating the details of the device selection step of the flowchart shown in FIG. 2.

As shown in FIG. 3, the device selection command step 104 includes a "table" selection command step 110, a "lighthead" selection command step 112, a "camera" selection command step 114, and a "task light" selection command step 116. In the control method, when the spoken word command "table" is received into the processing unit 34, the system is placed into a table command and actuation mode. Similarly, when a spoken word "lighthead" command, a spoken word "camera" command, or a spoken word "task light" command is received into the microphone 32, the system enters into a lighthead, camera, or task light command and execution mode, respectively. However, if no further commands are entered into the system within a predetermined delay period, preferably ten seconds, the system is reset in the first delay reset step 106. When this occurs, the operator must revocalize one of the "table", "lighthead", "camera", or "task light" command words to re-enter into the first delay reset step 106 in order to actuate a function selection command step 120.

FIGS. 4a–4d show detailed flowcharts illustrating the steps performed in the function selection command step 120. First, in the table mode of operation, the system is responsive to the spoken words "tilt", "Trendelenberg", "height", "back", "leg", "flex", "level", and "stop" for moving various portions of the surgical table 14. More particularly, in the table mode, the first function is responsive to the spoken word "tilt" at step 122 to laterally tilt the surgical table in a direction to be subsequently selected. At step 124, the system is responsive to the spoken word "Trendelenberg" to execute surgical table Trendelenberg motions in a direction to be subsequently selected. The third through eighth functions in the table mode of operation are based on system responsiveness to the spoken words "height", "back", "leg", "flex", "level", and "stop" for movement of selected portions of the surgical table in the vertical (height) direction, and in back and leg extension support members of the table.

Figure 4A:
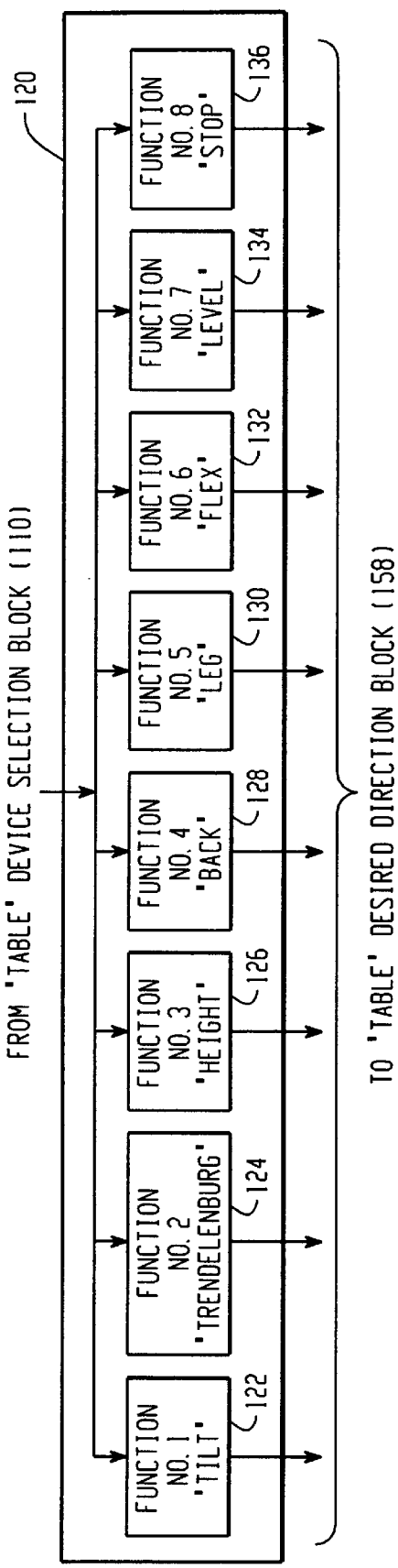
FIGS. 4a–4d are flowcharts illustrating the details of the function selection command step of the flowchart shown in FIG. 2.
Figure 4B:
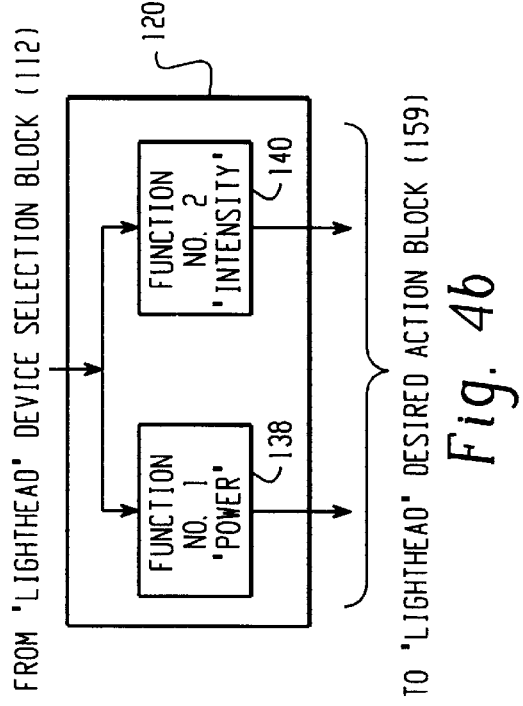

FIG. 4b shows a detailed flowchart of the function selection command step 120 performed when the system is in a lighthead mode of operation. More particularly, as shown there, the system is responsive to the spoken word "power" in step 138 for selective operation of the lighthead in a power ON or power OFF mode to be subsequently selected and to the spoken word "intensity" in step 140 for selective control over the intensity delivered by the lighthead 16.

Figure 4C:
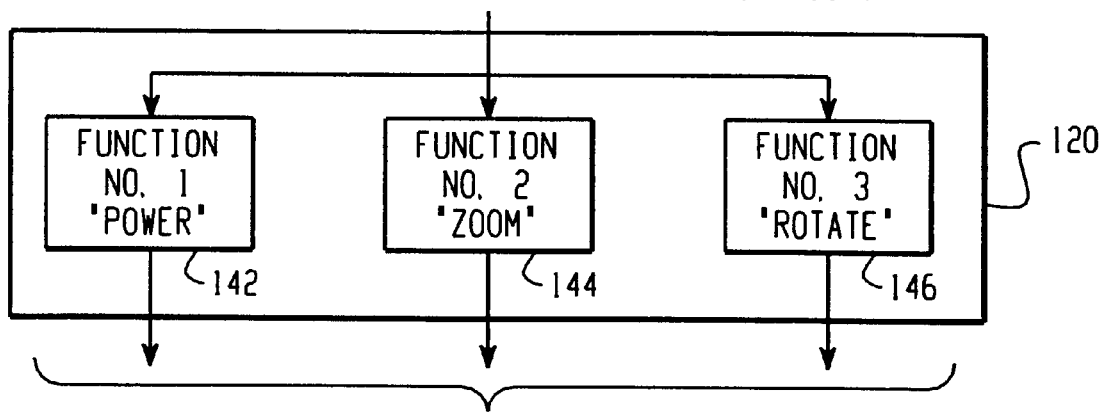

FIG. 4c shows a detailed flowchart illustrating the processing performed when the system is in a camera mode of operation. As shown there, the system is responsive to the spoken word "power" in step 142, to the spoken word "zoom" in step 144, and to the spoken word "rotate" in step 146.

Figure 4D:
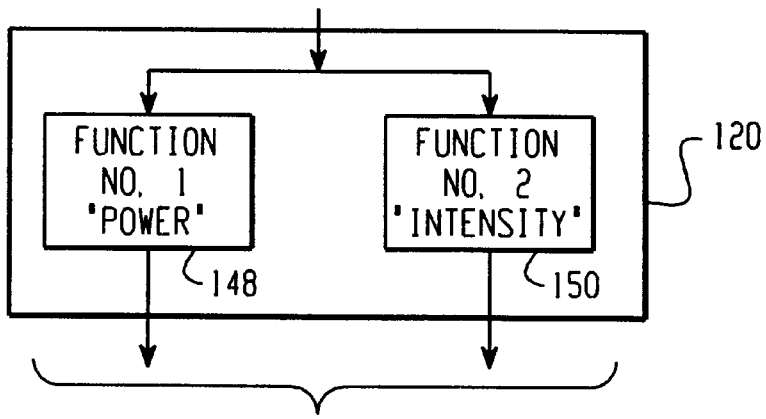

Lastly, at FIG. 4d, a detailed flowchart is illustrated showing the portion of the function selection command step 120 executed by the system when the system is in a task light mode of operation. At step 148, the system is responsive to the spoken word "power" for selectively controlling the task light power. At step 150 the system is responsive to the spoken word "intensity" to control the intensity of the task light to increase or decrease the intensity in a manner to be subsequently selected.

With reference yet once again to FIG. 2, a second delay reset step 150 is disposed in the control flow between the function selection command step 120 and the desired direction command step 152. In accordance with the invention, it is a benefit that the system returns to the previous control level when a desired direction command is not received within a predetermined time period, preferably seven seconds. As an example, when the system is in the surgical table control mode, and a spoken command "tilt" is received at step 122, the system begins a seven second delay counter. If a desired direction command is not received at step 152 within the seven second delay period, the "tilt" command is ignored and the system returned to the surgical table control mode at step 120. Thereafter, the surgeon can enter any one of the plurality of function selection commands including "tilt", "Trendelenberg", "height", "back", "leg", "flex", "level", or "stop". The system essentially "resets" itself so that mistaken commands can be easily corrected by merely pausing for the delay period, preferably seven seconds.

FIGS. 5a–5d illustrate a detailed flowchart of the command flow executed in the desired direction commands step 152. In the surgical table control mode at step 158, after the spoken function selection command "tilt" is inputted at step 122, the system is responsive to the spoken commands "right", "left", and "stop" at steps 160, 162, and 164 respectively to tilt the surgical table 14 to the right and left and to stop table motion. After the spoken word "Trendelenberg" is received into the system at step 124, the system is responsive to the spoken words "forward", "reverse" and "stop" at steps 166, 168, and 170 to cause the table to begin motion in the forward Trendelenberg and reverse Trendelenberg directions and to stop Trendelenburg table motion. At steps 172, 174, and 176 the system is responsive to the spoken words "up", "down", and "stop" after the spoken command "height" is inputted at step 126 to respectively raise the surgical table, lower the surgical table, and stop height motion. At steps 178, 180, and 182 the system is responsive to the spoken words "raise", "lower", and "stop" after the spoken word "back" is inputted at step 128. This portion of the control method 100 raises and lowers the back portion of the surgical table, respectively.

After the spoken word "leg" is inputted at step 130, the system is responsive to the spoken words "raise", "lower", and "stop" at steps 184, 186, and 188 to raise, lower, and stop movement of the leg portion of the surgical table, respectively. After the spoken word "flex" is inputted at step 132, the system is responsive to the spoken words "flex", "reflex", and "stop" at steps 190, 192, and 194 to flex the table, reflex the table, and stop movement, respectively. After the spoken word "level" is inputted at step 134, the system is responsive to the spoken words "return" and "stop" at steps 196 and 198 to return the table to level and to stop movement of the surgical table, respectively. Lastly, after the spoken word "stop" is inputted at step 136, the system is responsive to stop movement of the surgical table.

Figure 5A:
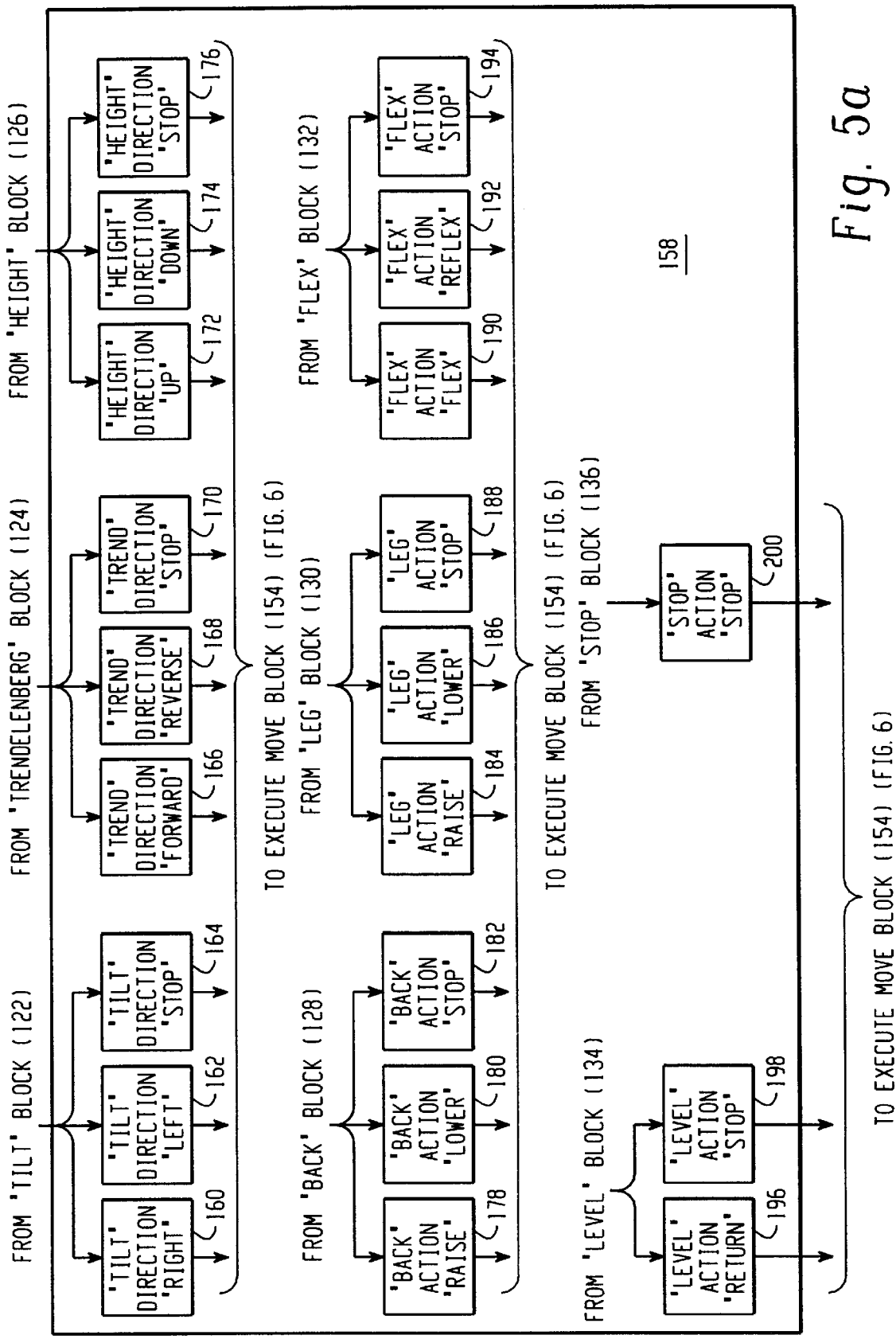
FIGS. 5a–5d are flowcharts illustrating the details of the desired direction command step shown in the flowchart of FIG. 2; and, FIG. 6 is a flowchart illustrating the details of the execute move command step in the flowchart of FIG. 2.
Figure 5B:
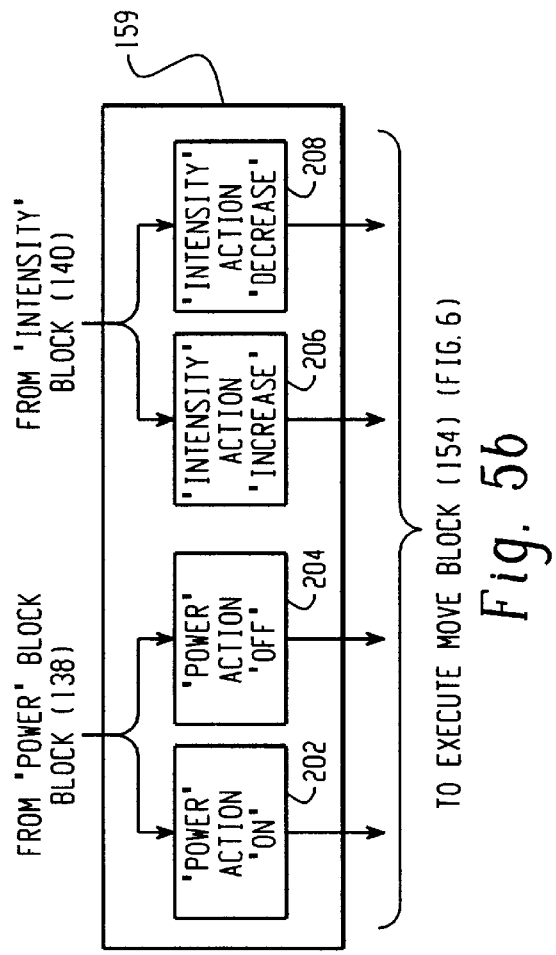

With reference next to FIG. 5b, the desired direction command step 152 includes the substeps of receiving a lighthead power "on" voice command signal at step 202 and a lighthead power "off" signal at step 204. Of course, the voice "on" and "off" commands are recognized by the processing unit 34 only when the system is in the lighthead mode subsequent to receiving a "lighthead" verbal command at step 112 in the device selection command step 104.

Figure 5C:
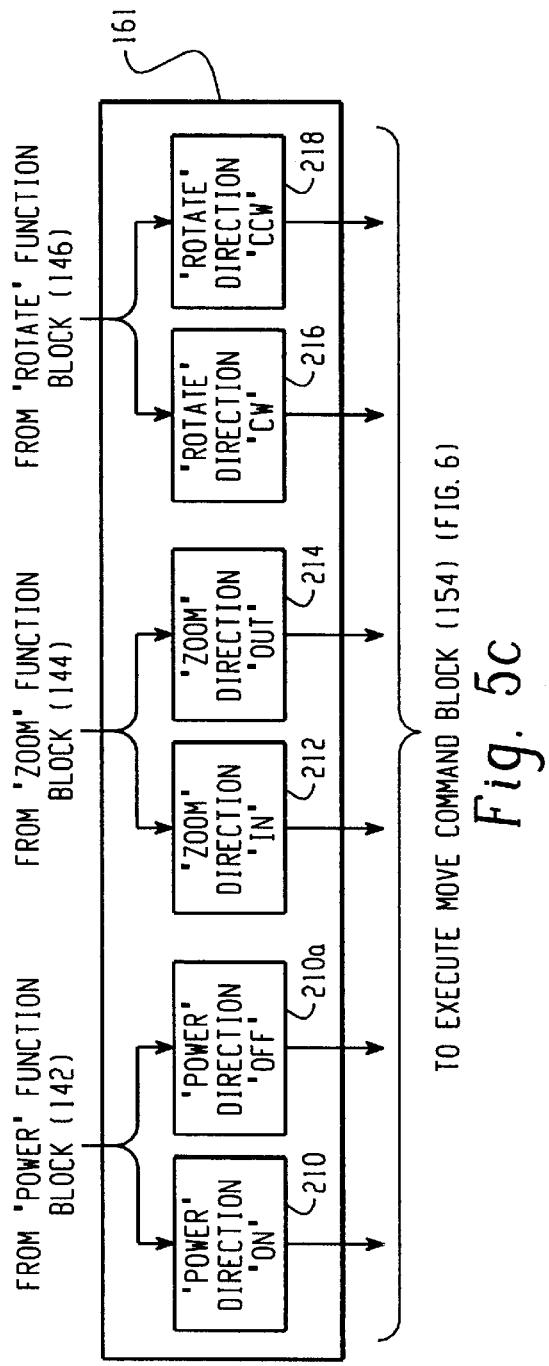

In FIG. 5c, the system is responsive to an "on" and an "off" command in steps 210 and 212 to turn the power on and off, respectively to the surgical camera 18. After the "camera" command is received at step 114 and the "zoom" command is received at step 144, the system is responsive to the commands "in" and "out" in steps 212 and 214 to cause the surgical camera 18 to zoom in and out, respectively. Lastly, with continued reference to FIG. 5c, after the command "camera" is received in step 114, and the function command "rotate" is received at step 146, the system is responsive to the verbal commands "clockwise" and "counter clockwise" at steps 216 and 218 to rotate the surgical camera 18 in the clockwise and counter clockwise directions, respectively.

Figure 5D:
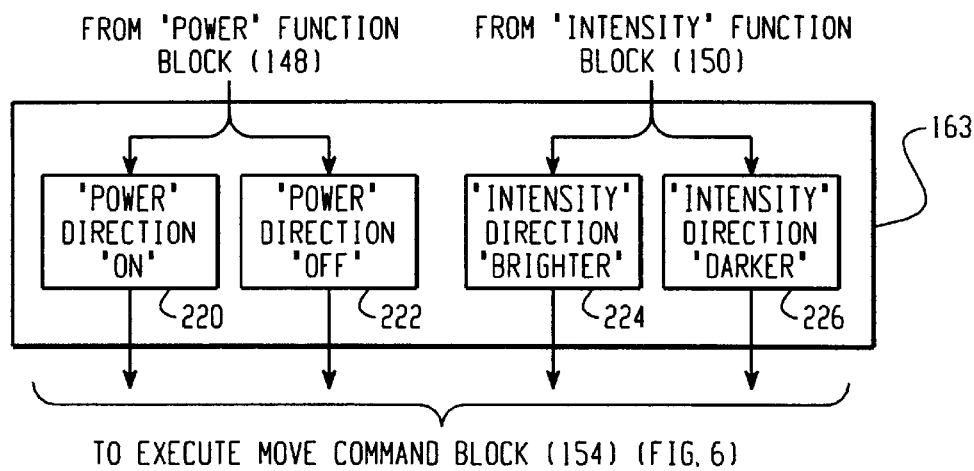

Turning next to FIG. 5d, in the task light mode, the system is responsive to the verbal commands "on" and "off" in steps 220 and 222 to turn the surgical task light on and off, respectively. Further, after the command "task light" is received into the system at step 116 and the command "intensity" is received into the system at step 150, the system is responsive to the audible commands "brighter" and "darker" at steps 224 and 226 to intensify and diminish the light intensity generated by the surgical task light 20, respectively.

Figure 6:
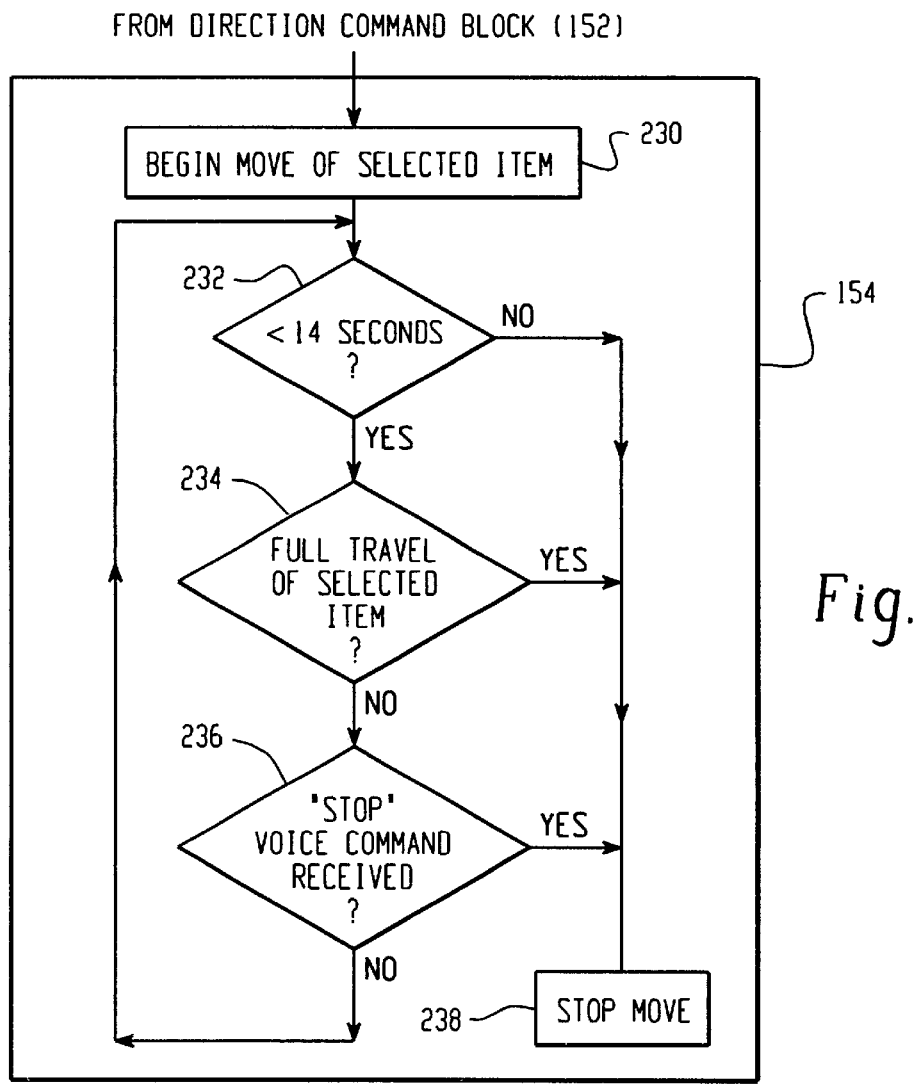

FIG. 6 is a detailed flowchart illustrating the execute move command step 154 executed by the system subsequent to the desired direction selection step 152. Preferably, in accordance with the present invention, movement of the selected item is commenced at step 230. As an added safety precaution, movement of physical items are performed for fourteen seconds or less. More particularly, at step 232, the fourteen second timer is compared and after fourteen seconds, the movement is terminated at step 238. When the movement is performed for less than fourteen seconds, the full travel of the selected items is interrogated at step 234. When the full travel has been met, the movement is terminated at step 238. Otherwise, the system awaits, in step 236, the receipt of an audible "stop" voice command whereupon when received, the system terminates the movement at step 238. Preferably, the system is responsive to any loud noise having sufficient power content or an excited utterance such as a loud shout at step 236 to stop movement or action at step 238.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is claimed:

1. A system for controlling a plurality of surgical apparatus comprising:

a control pendant manually operable to generate pendant command output signals;

a speech recognition device adapted to recognize a plurality of predetermined speech commands from a human operator and responsive to said set of predetermined speech commands to generate a set of speech command output signals;

a surgical table operatively connected with said speech recognition device and to said control pendant, the surgical table being responsive to both said pendant command output signals and to a first set of said speech command output signals to initiate selected surgical table movements;

a surgical lighthead operatively connected with said speech recognition device and responsive to a second set of said speech command output signals to initiate selected surgical lighthead operations; and, a surgical task light operatively connected with said speech recognition device and responsive to a third set of said speech command output signals to initiate selected surgical task light operations, wherein the surgical task light is supported by an associated mechanical member for movement into selected positions relative to said surgical table.

2. The system according to claim 1 wherein:

said speech recognition device is responsive to said set of predetermined speech commands from said human to generated at least one of: i) said first set of speech command output signals including a table raise signal, a table lower signal a Trendelenberg tilt signal, a reverse Trendelenberg tilt signal, a lateral tilt left signal, and a lateral tilt right signal, and ii) said second set of speech command output signals including a lighthead on signal and a lighthead off signal;

said surgical table is responsive to said table raise and lower signals to initiate table raise and lower motions, to said Trendelenberg and reverse Trendelenberg tilt signals to initiate table Trendelenberg motions, and to said lateral tilt left and right signals to initiate table lateral tilt motions; and, said surgical lighthead is responsive to said lighthead on and off signals to initiate and extinguish surgical lighthead operations, respectively.

3. The system according to claim 1 further including:

a surgical camera operatively connected with said speech recognition device and responsive to a third set of said speech command output signals to initiate selected surgical camera operations.

4. The system according to claim 3 wherein:

said speech recognition device is responsive to said set of predetermined speech commands from said human operator to generate: i) said first set of said speech command output signals including a camera zoom in signal, a camera zoom out signal, a camera rotate clockwise signal, and a camera rotate counter clockwise signal; and, said surgical camera is responsive to said camera zoom in and out signals to initiate camera zoom motion and to said camera rotate clockwise and counter clockwise signals to initiate camera rotation motion.

5. The system according to claim 3 wherein:

said speech recognition device is responsive to said set of predetermined speech commands from said human operator to generate at least one of: i) said first set of said speech command output signals including a table raise signal, a table lower signal, a Trendelenberg tilt signal, a reverse Trendelenberg tilt signal, a lateral tilt left signal, and a lateral tilt right signal, ii) said second set of speech command output signals including a lighthead on signal and a lighthead off signal, iii) said third set of speech command output signals including a surgical task light on signal and a surgical task light off signal, and iv) said fourth set of speech command output signals including a surgical camera zoom in signal, a surgical camera zoom out signal, a surgical camera rotate clockwise signal, and a surgical camera rotate counterclockwise signal;

said surgical table is responsive to said table raise and lower signals to initiate table elevate motions, to said table Trendelenberg and reverse Trendelenberg tilt signals to initiate table Trendelenberg motions, and to said lateral tilt left and right signals to initiate table lateral tilt motions;

said surgical lighthead is responsive to said surgical lighthead on and off signals to initiate and extinguish surgical lighthead operations, respectively;

said surgical camera is responsive to said surgical camera zoom in and out signals to initiate surgical camera zoom operations, and to said surgical camera rotate clockwise and counterclockwise signals to initiate surgical camera rotate motions: and, said surgical task light is responsive to said surgical task light on and off signals to initiate and extinguish surgical task light operations, respectively.

6. The system according to claim 3 further including:

a first remote control module connected to said surgical lighthead and manually operable to initiate said selected surgical lighthead operations;

a second remote control module connected to said surgical camera and manually operable to initiate said selected surgical camera operations; and, a third remote control module connected to said surgical task light and manually operable to initiate said selected surgical task light operations.

7. The system according to claim 1 wherein:

said speech recognition device is responsive to said set of predetermined speech commands from said single human to generate said third set of said speech command output signals including a task light on signal and a task light off signal; and, said surgical task light is responsive to said task light on and off signals to initiate and extinguish operation of said surgical task light.

8. The system according to claim 1 wherein:

said surgical table is adapted to respond exclusively to said pendant command output signals when both said pendant command output signals and said first set of said speech command output signals are present.

9. The system according to claim 1 further including:

a first remote control module connected to said surgical lighthead and manually operable to initiate said selected surgical lighthead operations.

10. The system according to claim 1 further including:

a surgical camera operatively connected with said speech recognition device and responsive to a fourth set of said speech command output signals to initiate selected surgical camera operations; and, a remote control module connected to said surgical camera and manually operable to initiate said selected surgical camera operations.

11. The system according to claim 1 further including;

a remote control module connected to said surgical task light and manually operable to initiate said selected surgical task light operations.

12. A method for voice controlling a plurality of surgical apparatus comprising:

providing a speech recognition device responsive to a set of predetermined voice commands from a human operator to generate a set of speech command output signals;

providing a control pendant manually operable to generate control pendant command output signals:

providing a surgical table operatively associated with said speech recognition device and responsive to: i) a first set of said speech command output signals to initiate selected surgical table movements, and ii) said control pendant command output signals to initiate said selected table movements:

providing a surgical lighthead operatively associated with said speech recognition system and responsive to a second set of said speech command output signals to initiate selected surgical lighthead operations;

providing a surgical task light operatively associated with said speech recognition device and responsive to a third set of said speech command output signals to initiate selected surgical task light operations, wherein the surgical task light is supported by an associated mechanical member for movement into selected positions relative to said surgical table;

receiving a first voice command from said human operator into the speech recognition system: and, based on said first voice command, generating, in the speech recognition system, a one of said first set of said speech command output signals and) said second set of said speech command output signals, and said third set of output signals, the first set of speech command output signals together with said control pendant command output signals for initiating said selected table movements said second set of speech command output signals for initiating said selected surgical lighthead operations, and said third set of speech command output signals for initiating selected surgical task light operations.

13. The method according to claim 12 further including the steps of:

providing a surgical camera operatively associated with said speech recognition device and responsive to a fourth set of said command output signals to initiate selected surgical camera operations;

receiving a second voice command from said human operator into the speech recognition system; and, based on said second voice command, generating, in the speech recognition system, a one of: i) said first set of said speech command output signals for initiating said selected surgical table movements, ii) said second set of said speech command output signals for initiating said selected surgical lighthead operations, and, iii) said fourth set of said speech command output signals for initiating said surgical camera operations.

14. The method according to claim 12 further including the steps of:

receiving a second voice command from said human operator into the speech recognition system; and, based on said second voice command, generating, in the speech recognition system, a one of: i) said first set of said speech command output signals for initiating said selected surgical table movements, ii) said second set of said speech command output signals for initiating said selected surgical lighthead operations, and iii) said third set of said speech command output signals for initiating said selected surgical task light operations.

15. The method according to claim 12 further including the steps of:

providing a surgical camera operatively associated with said speech recognition device and responsive to a fourth set of said speech command output signals to initiate selected surgical camera operations;

receiving a second voice command from said human operator into the speech recognition system; and, based on said second voice command, generating, in the speech recognition system, a one of: i) said first set of said speech command output signals for initiating said selected surgical table movements, ii) said second set of said speech command output signals or initiating said selected surgical lighthead operations, iii) said third set of said speech command output signals for initiating selected surgical task light operations, and iv) said fourth set of said speech command output signals for initiating said selected surgical camera operations.

16. The method according to claim 12 wherein:

the step of providing said surgical table includes providing a surgical table responsive exclusively to said control pendant command output signals to initiate said selected surgical table movements when both said speech command output signals and said control pendant command output signals are present.

* * * * *